US010118994B2

(12) United States Patent
Lang et al.

(10) Patent No.: US 10,118,994 B2
(45) Date of Patent: Nov. 6, 2018

(54) WATER SOLUBLE SILICONE MATERIAL

(71) Applicant: MOMENTIVE PERFORMANCE MATERIALS INC., Waterford, NY (US)

(72) Inventors: Weihong Lang, Niskayuna, NY (US); Wen P. Liao, Clifton Park, NY (US); Susan Nye, Feura Bush, NY (US); Kenrick M. Lewis, Flushing, NY (US)

(73) Assignee: MOMENTIVE PERFORMANCE MATERIALS INC., Waterford, NY (US)

( * ) Notice: Subject to any disclaimer, the term of this patent is extended or adjusted under 35 U.S.C. 154(b) by 0 days.

(21) Appl. No.: 14/765,054

(22) PCT Filed: Jan. 31, 2014

(86) PCT No.: PCT/US2014/014072
§ 371 (c)(1),
(2) Date: Jul. 31, 2015

(87) PCT Pub. No.: WO2014/121030
PCT Pub. Date: Aug. 17, 2014

(65) Prior Publication Data
US 2015/0368404 A1 Dec. 24, 2015

Related U.S. Application Data

(60) Provisional application No. 61/759,052, filed on Jan. 31, 2013.

(51) Int. Cl.
| G02B 1/04 | (2006.01) |
| C08G 77/44 | (2006.01) |
| C08G 77/442 | (2006.01) |
| C08G 77/46 | (2006.01) |
| A61F 2/00 | (2006.01) |
| C08F 283/12 | (2006.01) |
| C08F 290/06 | (2006.01) |
| A61L 27/18 | (2006.01) |
| A61L 29/06 | (2006.01) |
| C08L 83/10 | (2006.01) |
| A61F 2/16 | (2006.01) |
| A61B 17/00 | (2006.01) |

(52) U.S. Cl.
CPC ............. *C08G 77/44* (2013.01); *A61L 27/18* (2013.01); *A61L 29/06* (2013.01); *C08F 283/12* (2013.01); *C08F 290/068* (2013.01); *C08G 77/46* (2013.01); *C08L 83/10* (2013.01); *G02B 1/043* (2013.01); *A61B 2017/00942* (2013.01); *A61F 2/16* (2013.01)

(58) Field of Classification Search
CPC ...... C08G 77/44; C08G 77/442; C08G 77/46; G02B 1/043; C08F 283/12
USPC ................. 524/107, 105, 588; 523/107, 105
See application file for complete search history.

(56) References Cited

U.S. PATENT DOCUMENTS

| 4,152,508 | A | * | 5/1979 | Ellis | C08F 230/08 264/1.1 |
| 4,260,725 | A | | 4/1981 | Keogh et al. | |
| 4,486,577 | A | | 12/1984 | Mueller et al. | |
| 4,605,712 | A | * | 8/1986 | Mueller | C08F 290/148 351/159.33 |
| 5,219,965 | A | * | 6/1993 | Valint, Jr. | C08F 290/04 523/106 |
| 5,352,714 | A | | 10/1994 | Lai et al. | |
| 5,962,548 | A | | 10/1999 | Vanderlaan et al. | |
| 5,998,498 | A | | 12/1999 | Vanderlaan et al. | |
| 6,013,711 | A | | 1/2000 | Lewis et al. | |
| 6,207,782 | B1 | | 3/2001 | Czech et al. | |
| 6,867,245 | B2 | | 3/2005 | Iwata et al. | |
| 7,468,397 | B2 | | 12/2008 | Schorzman et al. | |
| 7,528,208 | B2 | | 5/2009 | Schorzman et al. | |
| 7,557,231 | B2 | | 7/2009 | Schorzman et al. | |
| 7,601,766 | B2 | | 10/2009 | Schorzman et al. | |
| 7,732,546 | B2 | | 6/2010 | Salamone et al. | |
| 7,759,408 | B2 | | 7/2010 | Schorzman et al. | |
| 7,781,558 | B2 | | 8/2010 | Schorzman et al. | |
| 7,825,273 | B2 | | 11/2010 | Schorzman et al. | |
| 7,960,447 | B2 | | 6/2011 | Schorzman et al. | |
| 7,960,465 | B2 | * | 6/2011 | Rathore | A61L 12/08 351/159.33 |
| 8,030,423 | B2 | | 10/2011 | Salamone et al. | |
| 8,048,968 | B2 | | 11/2011 | Phelan et al. | |
| 8,080,622 | B2 | | 12/2011 | Fujisawa et al. | |
| 8,129,442 | B2 | | 3/2012 | Ueyama et al. | |

(Continued)

FOREIGN PATENT DOCUMENTS

| JP | S61-145215 | 7/1986 |
| JP | H08-134153 | 5/1996 |

(Continued)

OTHER PUBLICATIONS

Patent Cooperation Treaty (PCT), International Search Report and Written Opinion for Application PCT/US14/14072 filed Jan. 31, 2014, dated Aug. 21, 2014, 9 pp., International Searching Authority, US.

*Primary Examiner* — Tae H Yoon
(74) *Attorney, Agent, or Firm* — Joseph Ostroff; McDonald Hopkins LLC

(57) ABSTRACT

A water soluble silicone macromer comprising a siloxane backbone having grafted thereto a suitable number of hydrophilic groups to render the macromer water soluble, the macromer comprising a polymerizable functional group grafted to the siloxane backbone. In one aspect, the present invention provides a water soluble silicone macromer having a structure of Formula (1): where M is a hydrophilic group or segment; L is a hydrophilic or hydrophobic linkage; N is a hydrophilic or hydrophobic group or segment. Q is a polymerizable functional group; x is zero or an integer greater than zero; y is zero or an integer greater than zero; v is zero or an integer greater than zero; and z is greater than zero, with the proviso that both y and v are not zero.

20 Claims, 1 Drawing Sheet

(56) References Cited

U.S. PATENT DOCUMENTS

| | | |
|---|---|---|
| 8,404,759 B2 | 3/2013 | Phelan |
| 8,404,783 B2 | 3/2013 | Chang et al. |
| 8,420,711 B2 * | 4/2013 | Awasthi ................ C08F 226/08 |
| | | 523/107 |
| 8,642,712 B2 | 2/2014 | Chang et al. |
| 8,686,099 B2 * | 4/2014 | Guyer ................... C07F 7/0852 |
| | | 523/105 |
| 8,828,420 B2 | 9/2014 | Schorzman et al. |
| 9,187,601 B2 | 11/2015 | Huang et al. |
| 2007/0161769 A1 | 7/2007 | Schorzman et al. |
| 2008/0004413 A1 | 1/2008 | Schorzman et al. |
| 2008/0021127 A1 | 1/2008 | Muller et al. |
| 2008/0076897 A1 | 3/2008 | Kunzler et al. |
| 2008/0076898 A1 | 3/2008 | Salamone et al. |
| 2011/0166248 A1 | 7/2011 | Hsu et al. |
| 2011/0181833 A1 * | 7/2011 | Guyer ................... C07F 7/0852 |
| | | 351/159.33 |

FOREIGN PATENT DOCUMENTS

| | | |
|---|---|---|
| JP | H11-181036 | 7/1999 |
| JP | H11-315142 | 11/1999 |
| JP | 2004-149592 | 5/2004 |
| JP | 2005-00350673 | 12/2005 |

* cited by examiner

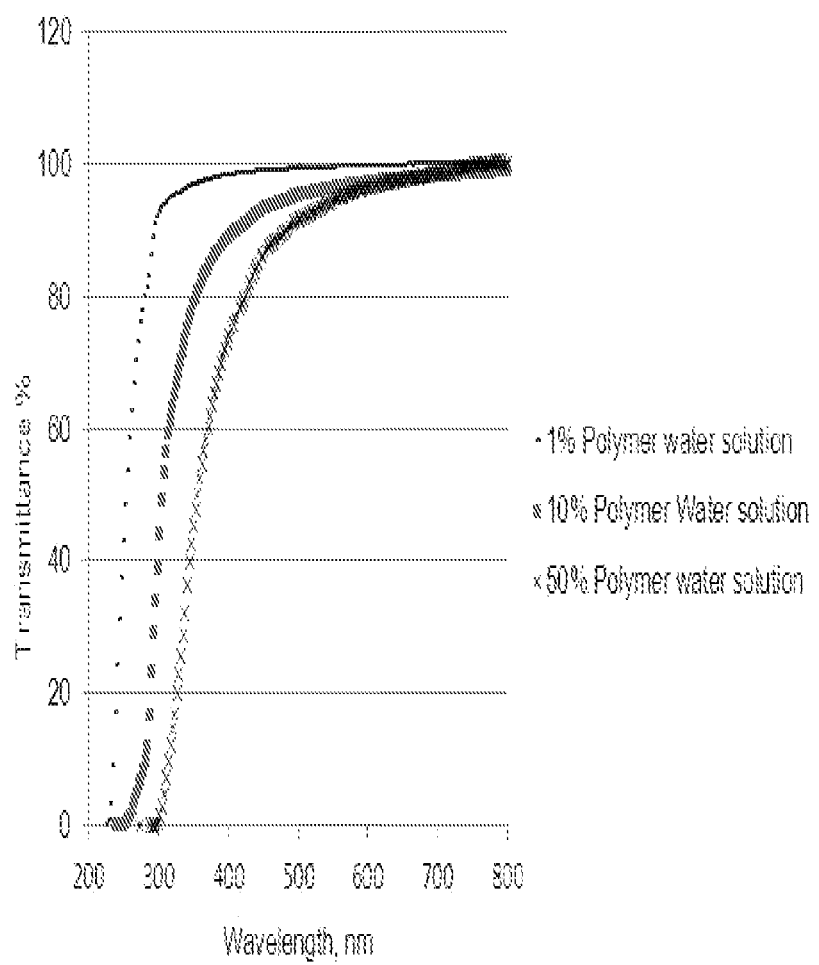

WATER SOLUBLE SILICONE MATERIAL

REFERENCE TO RELATED APPLICATIONS

The present application is a 35 U.S.C. 371 national stage filing and claims priority to PCT Application No. PCT/US2014/014072, entitled "Water Soluble Silicone Material," filed on Jan. 31, 2014, which claims the benefit of U.S. Provisional Application No. 61/759,052 filed on Jan. 31, 2013, both of which are incorporated herein by reference in their entirety.

FIELD

The present invention relates to a silicone macromer and polymers and hydrogels produced therefrom. The present invention provides, in one aspect, water soluble silicone macromers capable of undergoing free-radical polymerization. The present invention also relates to hydrogel compositions and films suitable for producing biomedical products including contact lenses.

BACKGROUND

A hydrogel is a hydrated, crosslinked polymeric system that contains water in an equilibrium state. Hydrogel contact lenses offer certain oxygen permeability as well as desirable biocompatibility and comfort. Conventional hydrogel materials (e.g. 2-hydroxyethylmethacrylate, HEMA) by themselves have poor oxygen permeability and they transport oxygen to the eye through the absorbed waterphase, but on the other hand due to the hydrophilic nature of the monomer, HEMA based lenses has better surface wettabilities which is very favorable for ophthalmic application. Silicone-hydrogels are used to make medical devices including implants and contact lenses of daily disposable and extended wear, as well as a group of rigid gas permeable lenses due to their relatively high oxygen permeability. Traditional siloxane monomers/polymers are hydrophobic and lenses made with them often require additional treatment for more hydrophilic surface. Many efforts were put into overcoming the hydrophobicity of the silicone materials.

Now silicone-hydrogels with the comfort of soft contact lenses and significantly higher oxygen permeability overcame the obstacles for periods of wear beyond conventional hydrogels and were revolutionary in the field of optometry. The following patents describe silicone-hydrogels for use in contact lenses.

U.S. Pat. No. 4,260,725 to Bausch & Lomb Inc., describes a water absorbing, soft, hydrophilic, flexible, hydrolytically stable, biologically inert contact lens with the capability of transporting oxygen sufficiently to meet the requirements of the human cornea comprising a polysiloxane which is α,ω terminally bonded through divalent hydrocarbon groups to polymerizably activated unsaturated groups and which contain hydrophilic side chains.

Water has low oxygen permeability, also called the Dk value, which may be expressed in Barrer, wherein 1 Barrer=$10^{-11}$ (cm$^3$ O$_2$) cm cm$^{-2}$ s$^{-1}$ mmHg$^{-1}$, "cm$^3$ O$_2$" is at a quantity of oxygen at standard temperature and pressure; "cm" represents the thickness of the material; and "cm$^{-2}$" is the reciprocal of the surface area of that material. The Dk of water is 80 Barrer. Upon exposure to atmospheric air for long periods, these lenses are slowly dehydrated and the amount of oxygen transported to the cornea is reduced. Eye irritation, redness and other corneal complications can result and hence restrict use of the lenses to limited periods of wear.

U.S. Pat. No. 5,352,714 also to Bausch & Lomb Inc. describes silicone-containing hydrogels with enhanced wettability comprising a silicone-containing monomer, hydrophilic monomers, and a relatively non-polar ring-containing monomer able to be converted to a highly polar amino acid upon hydration.

U.S. Pat. No. 5,998,498 to Johnson & Johnson Vision Products describes a silicone hydrogel prepared by curing a reaction mixture comprising a silicone-containing monomer having the following structure:

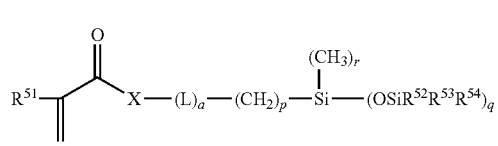

wherein $R^{51}$ is H or CH$_3$, q is 1 or 2 and for each q, $R^{52}$, $R^{53}$ and $R^{54}$ are independently ethyl, methyl, benzyl, phenyl or a monovalent siloxane chain comprising from 1 to 100 repeating Si—O units, p is 1 to 10, r=(3-q), X is O or NR$^{55}$, where $R^{55}$ is H or a monovalent alkyl group with 1 to 4 carbons, a is 0 or 1, and L is a divalent linking group which preferably comprises from 2 to 5 carbons, which may also optionally comprise ether or hydroxyl groups, for example, a polyethylene glycol chain.

U.S. Pat. No. 6,867,245 to Asahikasei Aime Co. describes a soft contact lens, and provides a contact lens that shows small and stable contact angle to water at its surface in water as well as in air, little deposition in wearing, high oxygen permeability, no adhesion of lens to a cornea, and superior extended-wearing characteristics. It describes a hydrogel soft contact lens, which has a contact angle at a lens surface in a range of 10-50° by the captive bubble method in water and 30-90° by the sessile drop method in air, oxygen permeability of not less than 30 and water content of not less than 5%, and also a hydrogel soft contact lens consisting of a polymer comprising a hydrophilic siloxanyl monomer shown by a specified general formula. This patent discloses copolymers of hydrophilic siloxane with amide-group containing monomers that are stated as being useful materials for contact lenses. The polymer comprises hydrophilic amide-group containing siloxanyl methacrylate, a siloxanyl methacrylate (tris[trimethylsiloxy]silylpropylmethacrylate, abbreviated as TRIS) including a hydrophilic polyether modified siloxanyl alkyl methacrylate and a crosslinkable monomer.

U.S. Pat. No. 6,013,711 to the CK Witco Corporation describes a method for improving the miscibility of the lower molecular weight unsaturated siloxane-polyether copolymers with the α,ω-divinylpolysiloxanes without loss of storage stability, or delay of cure at the vulcanization temperature, or loss of permanent hydrophilicity or other desirable features of the cured polysiloxane. The compositions comprise one or more α,ω-divinylpolysiloxanes, unsaturated polysiloxane-polyether copolymers having from 2 to 5 silicon atoms per molecule, which are preferably trisiloxanes, and a compatibilizing additive. The permanently hydrophilic, rapidly wettable polysiloxane compositions yield static water contact angles <50° and dynamic advancing contact angles of less than about 100.

U.S. Pat. No. 6,207,782 to Crompton Corporation discloses acrylated hydrophilic polysiloxane monomers and polymers and their copolymers with acrylate/methacrylate comonomers and their emulsions for personal care, textile and coating applications. The acrylated siloxanes are represented by formula (a):

$$[R_3SiO_{1/2}]_m[O_{1/2}SiR_2O_{1/2}]_n[SiO_{3/2}R]_o[SiO_{4/2}]_p \quad (a)$$

wherein R is selected from the $R^1$ and P, wherein each $R^1$ can be the same or different and each is a monovalent hydrocarbon group; each P is $R^3[O(C_bH_{2b}O)_zCOCR^4=CH_2]_g$ wherein, $R^3$ is a polyvalent organic moiety, which may be hydroxyl substituted alkylene, g is the valency of $R^3$ minus 1, $R^4$ is hydrogen or methyl; b=2 to 4, preferably 2 to 3; z=1 to 1000, preferably 3 to 30; and m+n+p+o=1 to 100, preferably 2 to 20, at least one R is P; n=1 to 100; when o is not zero n/o<10:1; when p is not zero n/p<10:1; and m=0 to 10. A preferred acrylated siloxane in the patent is of the Formula (b):

$$QR^1{}_2Si[OSiR^1{}_2]_x[O-SiR^1P]_yOSiR^1{}_2Q \quad (b)$$

wherein x, and y can be 0 or an integer, preferably each x and y are from 0 to 100, most preferably 0 to 25; Q can be $R^1$ or P, with the proviso that the average acrylate functionality is greater than 1 unsaturated groups per molecule with the preferred embodiment having y=0 and Q=P.

Conventionally, silicone-hydrogels are made by polymerizing the acrylate or methacrylate functionalized silicone monomer with hydrogel (hydrophilic) monomers, such as hydroxyethyl methacrylate (HEMA), N-Vinylpyrrolidone (NVP) and other monomers such as methyl methacrylic acid (MA), Dimethylacrylamide (DMA), etc, in the presence of crosslinker and thermal radical initiator or photoinitiators. Crosslinking agents generally have two or more reactive functional groups at different sites of the molecule. Typically, these sites contain polymerizable ethylenic unsaturation groups. During curing, they form a covalent bond with two different polymer chains and form a stable three-dimensional network to improve the strength of the polymer. Crosslinking agents conventionally used in contact lenses include ethylene glycol dimethacrylate and trimethyloylpropane trimethacrylate (about 0.1 to 2 wt %). Other useful crosslinking agents include diethyleneglycol dimethacrylate, bisphenol A dimethacrylate, diglycidyl bisphenol A dimethacrylate and dimethacrylate-terminated polyethylene glycol and reactive linear polyether modified silicones.

Generally, silicone hydrogel contact lens materials are made using hydrophobic mono-functional silicone monomer (such as TRIS) and/or difunctional hydrophilic silicone monomer followed by secondary surface treatment. The functionality of the siloxane monomers/polymers can affect the resulting silicone hydrogel's modulus.

The state of this art for soft contact lenses, including the silicone-based materials described in the above mentioned patents, still possess major shortfalls like sub-optimal surface wettability and lipid deposition. Silicone is an extremely hydrophobic material and difficult to modify to form a silicone-based material that is truly water soluble. U.S. Pat. No. 7,781,558 titled "Hydrophilic Siloxanyl Monomers With Pendant Polymerizable Groups" and U.S. Patent Publication No. 2008/0076898 entitled "Water Soluble Silicone Macromonomers for Ophthalmic Materials" describe incorporating ionic moieties into a polysiloxane side chain to impart hydrophilicity to the molecule and claim the formulation can possibly extracted by water. Still, the silicone or siloxane-based materials from the above patents are not fully water soluble.

Some silicone hydrogel materials are water dispersible and can be copolymerized with water-soluble organic monomers. However, materials that are water dispersible may not necessarily be fully water soluble. Non-fully water soluble monomers will likely require a non-water or non-aqueous solvent, or a compatibilizer such as a surfactant to ensure copolymerization. The solvent and compatibilizer must be removed, which increases manufacturing costs. Additionally, if the modified silicone monomer is not fully water-soluble, the silicone segment of the resulting polymer will aggregate into micelles in an aqueous medium, e.g., where contact lenses are stored and worn, in order to reduce free energy. In such conditions, silicone domains will have a minimum effect in improving oxygen permeability as the oxygen molecules will still need to transport through the aqueous medium, which has much lower oxygen solubility.

In an effort to overcome these drawbacks, current technology uses either expensive secondary surface treatments called "plasma oxidation" or use internal wetting agents. at relatively high manufacturing cost. Hence there remains a need for hydrophilic silicone monomers with inherently advantageous wettability and oxygen permeability that can be used to make contact lenses without the drawbacks and expensive surface treatments necessary with the silicone containing materials of the present art. When the material is highly water soluble, the formulation can be processed in water, this eliminates the use of organic solvent, compatilizer, surfactant in formulation and during extraction.

SUMMARY

In one aspect, the present invention provides a silicone macromer. In one embodiment, the silicone macromer comprises a siloxane backbone having grafted thereto a suitable number of hydrophilic groups to render the macromer at least partially hydrophilic. In one embodiment, the macromer comprises a polymerizable functional group grafted to the siloxane backbone. In one embodiment, the silicone macromer is water soluble.

In one aspect, the present invention provides a silicone macromer having a structure of Formula (1):

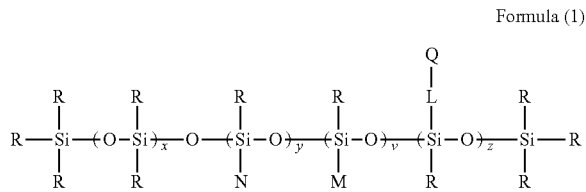

Formula (1)

where M is a hydrophilic group or segment; L is a hydrophilic or hydrophobic linkage; N is a hydrophilic or hydrophobic group or segment. Q is a polymerizable functional group; x is zero or an integer greater than zero; y is zero or an integer greater than zero; v is zero or an integer greater than zero; and z is greater than zero, with the proviso that y and v are not both zero. In one embodiment, the L group can a hydrophilic linkage and can be the same as or different than the hydrophilic M group.

The L group can form a linkage between the siloxane backbone and the polymerizable functional group Q. The L group can be a hydrophilic or hydrophobic linkage. In one embodiment, L can be chosen from a group including, but not limited to, a bond, a straight or branched C1-C30 alkyl group, a C1-C30 fluoroalkyl group, a C1-C20 ester-containing group, an alkyl ether, cycloalkyl ether, cycloalkenyl ether, aryl ether, arylalkyl ether, a polyether-containing group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, a C5-C30 fluoroaryl group, a hydroxyl substituted alkyl ether, and combinations of two or more thereof. L can also be a substituted or unsubstituted C3-C30 cationic moiety containing group.

In one embodiment, the polymerizable functional group Q can be an ethylenically unsaturated organic radical. Examples of suitable polymerizable groups include, but are not limited to, acrylate-containing radicals, methacrylate-containing radicals, acrylamide-containing radicals, methacrylamide-containing radicals, vinyl-containing radicals, allyl-containing radicals, methallyl-containing radicals, styrene-containing radicals, internal olefinic bond containing molecules, etc. Vinyl-containing radicals can include vinylcarbonate-containing radicals, vinylcarbamate-containing radicals, etc. Examples of internal olefinic bond containing molecules include butenedioic acid, butenedioic esters or amides, itaconic acid, itaconic acid esters or amides, etc.

In one embodiment, the Q group can comprise a hydrophilic molecule. Suitable hydrophilic molecules include, but are not limited to, hydroxyl-substituted lower alkyl acrylates and methacrylates, acrylamide, methacrylamide, lower alkylacrylamides and methacrylamides, ethoxylated acrylates and methacrylates, hydroxyl-substituted lower alkylacrylamides and methacrylamides, hydroxyl-substituted lower alkyl vinyl ethers, sodium vinylsulfonate, sodium styrenesulfonate, 2-acrylamido-2-methyl-propanesulfonic acid, N-vinylpyrrole, N-vinyl-2-pyrrolidone, 2-vinyloxazoline, 2-vinyl-4,4'-di-alkyloxazolin-5-one, 2- and 4-vinylpyridine, vinylically unsaturated carboxylic acids having a total of 3 to 5 carbon atoms, amino-lower alkyl (where the term "amino" also includes quaternary ammonium), mono-lower alkylamino-lower alkyl and di-lower alkylamino-lower alkyl acrylates and methacrylates, allyl alcohol and the like. Particularly suitable hydrophilic molecules include, for example, N-vinyl-2-pyrrolidone, acrylamide, methacrylamide, hydroxyl-substituted lower alkyl acrylates and methacrylates, hydroxyl-substituted lower alkylacrylamides and -methacrylamides and vinylically unsaturated carboxylic acids having a total of 3 to 5 carbon atoms.

In one embodiment, the hydrophilic group M is chosen from a small molecule, a polymer, or a combination thereof. In one embodiment, M is chosen from a polyvinyl alcohol (PVA), a polyglycerol methacrylate, a polyamide, a polyimide, a polylactone, a homopolymer of a vinyl lactam, a copolymer of at least one vinyl lactam in the presence or in the absence of one or more vinylic comonomers, a homopolymer of acrylamide, a homopolymer of methacrylamide, a copolymer of acrylamide with one or more hydrophilic vinylic monomers, a copolymer methacrylamide with one or more hydrophilic vinylic monomers, polyethylene oxide, a polyoxyethylene derivative, a poly-N—N dimethylacrylamide, a polyacrylic acid, a poly-2-ethyl oxazoline, a heparin polysaccharides, a polysaccharide, or a combination of two or more thereof. In one embodiment, M is chosen from a small molecule such as, but not limited to, vinyl pyrrolidone, 2-hydroxyethyl methacrylate, dimethyl acrylamide, glycerol methacrylate, substituted or unsubstituted vinyl containing straight or branched ester containing molecules, substituted or unsubstituted vinyl containing straight or branched alkyl ether, substituted or unsubstituted vinyl containing straight or branched C2-C10 heteroaryl molecules, substituted or unsubstituted vinyl containing straight or branched C2-C10 heterocyclic ring, substituted or unsubstituted vinyl containing straight or branched C2-C10 heterocyclicalkyl molecules. M can also be a substituted or unsubstituted straight or branched C3-C30 cationic moiety containing group.

In one embodiment, N group can be hydrophilic or hydrophobic, can be a polymer or a small molecule that linked to the polysiloxane back bone. N can be the same or different from M. N can be chosen from a group including, but not limited to, a bond, a straight or branched C1-C30 alkyl group, a C1-C30 fluoroalkyl group, a C1-C20 ester-containing group, an alkyl ether, cycloalkyl ether, cycloalkenyl ether, aryl ether, arylalkyl ether, a polyether-containing group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, a C5-C30 fluoroaryl group, a hydroxyl substituted alkyl ether, and combinations of two or more thereof. N can also be a substituted or unsubstituted C3-C30 cationic moiety containing group.

In one embodiment, z in the macromer of formula 1 is greater than zero. In one embodiment, z is an integer from 1 to 200; from 2 to 100; from 3 to 50; even from 5 to 25. In one embodiment, z is from 1 to 50. In one embodiment, x can be 0 or an integer greater than zero. In one embodiment, x can be 0 to about 1000; from about 2 to about 500; from about 3 to about 200; even from about 4 to about 100; even from about 5 to about 50. In one embodiment, y can be 0 or an integer greater than zero. In one embodiment, y can be 0 to about 200; from about 2 to about 100; from about 3 to about 50; even from about 4 to about 25. In one embodiment, v can be 0 or an integer greater than zero. In one embodiment, v can be 0 to about 200; from about 2 to about 100; from about 3 to about 50; even from about 4 to about 25.

In one embodiment, the macromer can comprise ionic moieties.

In one aspect, the present invention provide compositions, e.g., hydrogel forming compositions, comprising the macromer, optionally a comonomer, and/or optionally water.

In one aspect, the present invention provides a hydrogel comprising a water soluble macromer in accordance with aspects of the present invention.

In one embodiment, the hydrogel absorbs about 10 wt. % to 90 wt. % of water; about 20 wt. % to about 80 wt. % of water; about 30 wt. % to about 75 wt. % of water; even about 40 wt. % to about 60 wt. % of water.

In one embodiment, the hydrogel surface has a contact angle with water of about 100° to about 5°; from about 90° to about 10°; from about 80° to about 20°; even from about 70° to about 30°. In one embodiment, the hydrogel has a contact angle with water of from about 5° to about 25°.

In one aspect, the present invention provides an article formed from a material comprising a hydrophilic macromer, in one embodiment, a water soluble macromer in accordance with aspects of the invention. In one embodiment, the article is a medical device. In one embodiment, the medical device is chosen from heart valves and films, surgical devices, vessel substitutes, intrauterine devices, membranes, diaphragms, surgical implants, blood vessels, artificial ureters, artificial breast tissue, membranes for kidney dialysis and heart/lung machines, catheters, mouth guards, denture liners, ophthalmic devices, contact lenses, etc.

The present invention provides, in one aspect, a highly water soluble silicone material. The water soluble macromer provides a material that allows for the transport of oxygen through substantially the entire length or backbone of the macromer or hydrogel formed therefrom. The fully water soluble macromer avoids problems associated with polymers that are not fully water soluble, e.g., the aggregation of the polymer into micelles, which can cause lower oxygen permeability. Further, unlike water processible polymers, macromers in accordance with aspects of the invention can be processed or polymerized without the need for solvents or compatiblizers.

In one aspect, the present invention provides, a silicone material wherein the silicone material is water soluble, and satisfies at least one of the following criteria: (a) 1% of the silicone material in a water solution has a transparency of 80% or greater on UV VIS between 400 to 600 nm; (b) 10% of the silicone material in a water solution has a transparency of 80% or greater on UV VIS between 400 to 600 nm; (c) 50% of the silicone material in a water solution has a transparency of 80% or greater on UV VIS between 400 to 600 nm; and/or (d) 1% of the silicone material in a water solution has a cloud point of over 30° C.

In one embodiment, a hydrogel formed from a macromer in accordance with the present invention provides for improved processability as residual silicone, if any is present, can be extracted with water. In another embodiment, a hydrogel formed from a macromer in accordance with the present invention can be processed without requiring any additional extractions. Further, articles formed from hydrogels in accordance with the present invention can be provided without any additional surface treatments that are employed in conventional hydrogels or articles to improve wetting.

In still another aspect, the present invention provides a hydrogel formed from a hydrogel forming composition comprising at least one siloxane material with crosslinkable function, comprises from 0.1 weight percent to about 90 weight percent of water. In one embodiment, the present invention provides a hydrogel formed from a hydrogel forming composition comprising at least one siloxane material with crosslinkable function, comprises from 1 weight percent to about 70 weight percent of water. In still another embodiment, the present invention provides, a hydrogel formed from a hydrogel forming composition comprising at least one siloxane material with crosslinkable function, comprises from 5 weight percent to about 50 weight percent of water. In yet another embodiment, the present invention provides, a hydrogel formed from a hydrogel forming composition comprising at least one siloxane material with crosslinkable function, comprises from 10 weight percent to about 30 weight percent of water.

These and other aspects and embodiments can be further understood with reference to the following detailed description.

BRIEF DESCRIPTION OF THE DRAWINGS

FIG. 1 is a UV Vis spectra of the polymer solutions of Example 10.

DETAILED DESCRIPTION

In accordance with aspects of the present invention, new hydrophilic, silicone macromers are useful for preparing water-absorbing silicone hydrogel films that can be used in contact lens applications are described. The silicone macromers comprise a polysiloxane backbone and a sufficient concentration of hydrophilic polyether grafts to impart water solubility to the macromer. Silicone hydrogel films obtained with these monomers can show excellent wettability in comparison to previously known films. The hydrogel films may also exhibit improved oxygen permeability and modulus.

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

A "macromer" refers to a medium and high molecular weight compound that can comprise one or more functional groups capable of being polymerized, crosslinked, or both.

A "monomer" refers to a relatively low molecular weight compound that is polymerizable.

A "hydrophilic" substance (e.g., hydrophilic monomer, hydrophilic macromer, hydrophilic polymer, etc.) is one that is water-loving, has an affinity for water, is capable of absorbing water, etc. A hydrophilic substance may be soluble or insoluble (e.g., substantially insoluble) in water. A hydrophilic substance can, in one embodiment, contain both hydrophilic and hydrophobic portions, but the hydrophobic portions are present in relative amounts such that the substance or component is hydrophilic. In one embodiment, a hydrophilic substance can absorb at least 10 percent by weight water.

A "hydrophobic" substance (e.g., hydrophobic monomer, hydrophobic segment, etc.) is one that is generally water insoluble. A hydrophobic substance can, in one embodiment, contain both hydrophobic and hydrophilic portions, but the hydrophilic portions are present in relative amounts such that the substance or component is hydrophilic. In one embodiment, a hydrophilic substance can absorb less than 10% by weight of water.

"Homopolymers" are polymers made from the same repeating macromer or monomer. "Copolymers" are polymers wherein the polymer contains at least two structurally different macromers, at least two structurally monomers, or at least one macromer and at least one monomer. Notations such as (meth)acrylate denote monomer with either acrylate or methacrylate functionality.

The present invention provides a polymerizable hydrophilic silicone macromer. The macromers comprise a polysiloxane backbone comprising a hydrophilic polyether group pendant to the polysiloxane backbone. The macromer comprises a sufficient number of hydrophilic polyether pendant groups to render the macromer hydrophilic. The macromer further comprises a polymerizable functional group grafted to the polysiloxane backbone. In one embodiment, the polymerizable functional group can be directly grafted to the polysiloxane backbone. In one embodiment, the polymerizable functional group can be provided as part of the polyether pendant groups, and can be provided by endcapping the polyether pendant group with the polymerizable functional group. In one embodiment, at least one polyether graft per chain (or macromer unit) comprises a polymerizable group.

The macromers comprise a hydrophilic group to render the macromer hydrophilic. It will be appreciated that the macromer can be non-water soluble, partially water soluble, even highly water soluble.

In one embodiment, the water soluble silicone macromer has a structure of Formula (1):

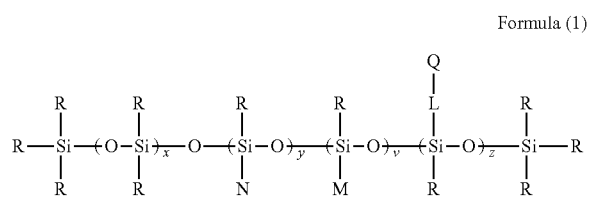

Formula (1)

where M is a hydrophilic segment; N is a hydrophilic or hydrophobic group; L is a hydrophilic or hydrophobic linkage; Q is a polymerizable functional group; x is zero or an integer greater than zero; y is zero or an integer greater than zero; v is zero or an integer greater than zero; and z is greater than zero with the proviso that y and v are not both zero. The M, N and L group can be the same or different.

The L group can form a linkage between the between the siloxane backbone and the polymerizable functional group Q. The L group can be a hydrophilic or hydrophobic linkage. In one embodiment, the L group can be a hydrophilic linkage or group. When the L group is a hydrophilic linkage, the L group can be the same as or different than the M group.

In one embodiment, L can be chosen from a group including, but not limited to, a bond, a straight or branched C1-C30 alkylene group, a C1-C30 fluoroalkylene group, a C1-C20 ester-containing group, an alkylene ether, cycloalkylene ether, cycloalkenylene ether, arylene ether, arylalkylene ether, a polyether-containing group, a substituted or unsubstituted C1-C30 alkoxy group, a substituted or unsubstituted C3-C30 cycloalkylene group, a substituted or unsubstituted C3-C30 cycloalkylalkylene group, a substituted or unsubstituted C3-C30 cycloalkenylene group, a substituted or unsubstituted C5-C30 arylene group, a substituted or unsubstituted C5-C30 arylalkylene group, a substituted or unsubstituted C5-C30 heteroarylene group, a substituted or unsubstituted divalent C3-C30 heterocyclic ring, a substituted or unsubstituted C4-C30 heterocycloalkylene group, a substituted or unsubstituted C6-C30 heteroarylalkylene group, a C5-C30 fluoroarylene group, a hydroxyl substituted alkylene ether, a divalent C3-C30 cationic moiety containing group; and combinations of two or more thereof.

In one embodiment, the L group can be chosen from a hydrophobic molecule. The hydrophobic molecule can be chosen from C1-C18 alkyl and C3-C18 cycloalkyl acrylates and methacrylates, C3-C18 alkylacrylamides and -methacrylamides, acrylonitrile, methacrylonitrile, vinyl C1-C18 alkanoates, C2-C18 alkenes, C2-C18 haloalkenes, styrene, lower alkyl styrene, lower alkyl vinyl ethers, C2-C10 perfluoroalkyl acrylates and methacrylates or correspondingly partly fluorinated acrylates and methacrylates, C3-C12 perfluoroalkyl-ethyl-thiocarbonylaminoethyl acrylates and methacrylates, acryloxy- and methacryloxy-alkylsiloxanes, N-vinylcarbazole and C1-C12 alkyl esters of maleic acid, fumaric acid, itaconic acid, mesaconic acid, etc. Other examples include, for example, acrylonitrile, C1-C4 alkyl esters of vinylically unsaturated carboxylic acids having 3 to 5 carbon atoms, or vinyl esters of carboxylic acids having up to 5 carbon atoms.

Examples of suitable hydrophobic molecules can include, but are not limited to, methyl acrylate, ethyl acrylate, propyl acrylate, isopropyl acrylate, isobutyl acrylate (IBA), isooctyl acrylate (OA), isodecyl acrylate (DA), cyclohexyl acrylate, 2-ethylhexyl acrylate (EHA), methyl methacrylate, ethyl methacrylate, propyl methacrylate, butyl acrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl (meth)acrylate (HFBMA and HFBA), tris-trimethylsilyloxy-silyl-propyl methacrylate (TRIS), 3-methacryloxypropylpentamethyldisiloxane, and bis(methacryloxypropyl) tetramethyldisiloxane.

In one embodiment, the L group can comprise a hydrophilic group or molecule. The hydrophilic group or segment can be a short or long chain polymer segment as desired. Suitable hydrophilic molecules include, but are not limited to, hydroxyl-substituted lower alkyl acrylates and methacrylates, acrylamide, methacrylamide, lower alkylacrylamides and methacrylamides, ethoxylated acrylates and methacrylates, hydroxyl-substituted lower alkylacrylamides and methacrylamides, hydroxyl-substituted lower alkyl vinyl ethers, sodium vinylsulfonate, sodium styrenesulfonate, 2-acrylamido-2-methyl-propanesulfonic acid, N-vinylpyrrole, N-vinyl-2-pyrrolidone, 2-vinyloxazoline, 2-vinyl-4,4'-di-alkyloxazolin-5-one, 2- and 4-vinylpyridine, vinylically unsaturated carboxylic acids having a total of 3 to 5 carbon atoms, amino-lower alkyl (where the term "amino" also includes quaternary ammonium), mono-lower alkylamino-lower alkyl and di-lower alkylamino-lower alkyl acrylates and methacrylates, allyl alcohol and the like. Particularly suitable hydrophilic molecules include, for example, N-vinyl-2-pyrrolidone, acrylamide, methacrylamide, hydroxyl-substituted lower alkyl acrylates and methacrylates, hydroxyl-substituted lower alkylacrylamides and -methacrylamides and vinylically unsaturated carboxylic acids having a total of 3 to 5 carbon atoms.

Examples of suitable hydrophilic polymers for the L group include, but are not limited to, polyvinyl alcohols (PVAs), polyamides, polyimides, polylactone, a homopolymer of a vinyl lactam, a copolymer of at least one vinyl lactam in the presence or in the absence of one or more vinylic comonomers, a homopolymer of acrylamide or methoacrylamide, a copolymer of acrylamide or methoacrylamide with one or more hydrophilic vinylic monomers, polyethylene oxide (i.e., polyethylene glycol (PEG)), a polyoxyethylene derivative, poly-N—N dimethylacrylamide, polyacrylic acid, poly 2 ethyl oxazoline, heparin polysaccharides, polysaccharides, and mixtures thereof.

Still other examples of suitable hydrophilic molecules include, but are not limited to, hydroxyethyl methacrylate (HEMA), hydroxyethyl acrylate, hydroxypropyl acrylate, trimethylammonium-2-hydroxypropyl methacrylate hydrochloride (Blemer® QA, for example from Nippon Oil), dimethylaminoethyl methacrylate (DMAEMA), dimethylaminoethyl methacrylamide, acrylamide, methacrylamide, N,N-dimethylacrylamide (DMA), allyl alcohol, vinylpyridine, glycerol methacrylate, N-(1,1-dimethyl-3-oxobutyl) acrylamide, N-vinyl-2-pyrrolidone (NVP), acrylic acid, methacrylic acid, etc.

The Q group can be any suitable polymerizable group. In one embodiment, the polymerizable functional group Q can be an ethylenically unsaturated organic radical. Examples of suitable polymerizable groups include, but are not limited to, acrylate-containing radicals, methacrylate-containing radicals, acrylamide-containing radicals, methacrylamide-containing radicals, vinyl-containing radicals, allyl-containing radicals, methallyl-containing radicals, styrene-containing radicals, internal olefinic bond containing molecules, etc. Vinyl-containing radicals can include vinylcarbonate-containing radicals, vinylcarbamate-containing radicals, etc. Examples of internal olefinic bond containing molecules include butenedioic acid, butenedioic esters or amides, itaconic acid, itaconic acid esters or amides, etc. In one embodiment, the polymerizable group comprises a group having the general structure of Formula 2:

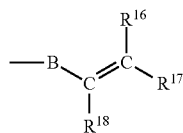

(2)

wherein B is a divalent radical containing 1 to 20 carbon atoms and can optionally contain heteroatoms such as O and N, etc; $R^{16}$, $R^{17}$ and $R^{18}$ are independently hydrogen, substituted or unsubstituted monovalent radicals. In one embodiment, the monovalent radicals can be chosen from a substituted or unsubstituted saturated monovalent hydrocarbon group of 1 to about 20 carbons.

The M group comprises a hydrophilic segment or molecule. The hydrophilic segment M can be any suitable hydrophilic molecule, including those hydrophilic groups or molecules suitable as the L group. Suitable hydrophilic molecules include, but are not limited to, hydroxyl-substituted lower alkyl acrylates and methacrylates, acrylamide, methacrylamide, lower alkylacrylamides and -methacrylamides, ethoxylated acrylates and methacrylates, hydroxyl-substituted lower alkylacrylamides and -methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-di-alkyloxazolin-5-one, 2- and 4-vinylpyridine, vinylically unsaturated carboxylic acids having a total of 3 to 5 carbon atoms, amino-lower alkyl (where the term "amino" also includes quaternary ammonium), mono-lower alkylamino-lower alkyl and di-lower alkylamino-lower alkyl acrylates and methacrylates, allyl alcohol and the like. Exemplary hydrophilic molecules include, for example, N-vinyl-2-pyrrolidone, acrylamide, methacrylamide, hydroxyl-substituted lower alkyl acrylates and methacrylates, hydroxyl-substituted lower alkylacrylamides and -methacrylamides and vinylically unsaturated carboxylic acids having a total of 3 to 5 carbon atoms.

Examples of suitable hydrophilic polymers, for the M group include, but are not limited to, polyvinyl alcohols (PVAs), polyamides, polyimides, polylactone, a homopolymer of a vinyl lactam, a copolymer of at least one vinyl lactam in the presence or in the absence of one or more vinylic comonomers, a homopolymer of acrylamide or methacrylamide, a copolymer of acrylamide or methacrylamide with one or more hydrophilic vinylic monomers, polyethylene oxide (i.e., polyethylene glycol (PEG)), a polyoxyethylene derivative, poly-N—N dimethylacrylamide, polyacrylic acid, poly 2 ethyl oxazoline, heparin polysaccharides, polysaccharides, and mixtures of two or more thereof.

Examples of suitable hydrophilic molecules for the M group include, polyethylene glycol, hydroxyethyl methacrylate (HEMA), hydroxyethyl acrylate, hydroxypropyl acrylate, trimethylammonium-2-hydroxypropyl methacrylate hydrochloride (Blemer®.QA, for example from Nippon Oil), dimethylaminoethyl methacrylate (DMAEMA), dimethylaminoethyl methacrylamide, acrylamide, methacrylamide, N,N-dimethylacrylamide (DMA), allyl alcohol, vinylpyridine, glycerol methacrylate, N-(1,1-dimethyl-3-oxobutyl)acrylamide, N-vinyl-2-pyrrolidone (NVP), acrylic acid, methacrylic acid and the like.

In one embodiment, N group can be hydrophilic or hydrophobic, can be a polymer or a small molecule that linked to the polysiloxane back bone. N can be the same or different from M. N can be chosen from a group including, but not limited to, a bond, a straight or branched C1-C30 alkyl group, a C1-C30 fluoroalkyl group, a C1-C20 ester-containing group, an alkyl ether, cycloalkyl ether, cycloalkenyl ether, aryl ether, arylalkyl ether, a polyether-containing group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, a C5-C30 fluoroaryl group, a hydroxyl substituted alkyl ether, and combinations of two or more thereof. N can also be a substituted or unsubstituted C3-C30 cationic moiety containing group.

The water soluble macromers comprise at least one graft segment comprising a polymerizable functional group (e.g., at least one -L-Q group). Thus, in one embodiment, z in the macromer of formula 1 is greater than zero. In one embodiment, z is an integer from 1 to 200; from 2 to 100; from 3 to 50; even from 5 to 25. Here as elsewhere in the specification and claims, numerical values can be combined to form new and non-disclosed ranges.

In the macromer of Formula 1, x can be 0 or an integer greater than zero. In one embodiment, x can be 0 to about 1000; from about 2 to about 500; from about 3 to about 200; even from about 5 to about 50. Here as elsewhere in the specification and claims, numerical values can be combined to form new and non-disclosed ranges.

In the macromer of Formula 1, y can be 0 or an integer greater than zero. In one embodiment, y can be 0 to about 200; from about 2 to about 100; from about 3 to about 50; even from about 4 to about 25. Here as elsewhere in the specification and claims, numerical values can be combined to form new and non-disclosed ranges. As described above, y and v are not both zero, and the macromer comprises at least one y and/or at least one v unit.

The R groups are not particularly limited and can be chosen as desired for a particular purpose or intended use. In one embodiment, R is independently hydrogen, a straight or branched C1-C30 alkyl group, a C1-C30 fluoroalkyl group, a C1-C20 ester-containing group, an alkyl ether, cycloalkyl ether, cycloalkenyl ether, aryl ether, arylalkyl ether, a polyether-containing group, a substituted or unsubstituted C1-C30 alkoxy group, a substituted or unsubstituted C3-C30 cycloalkyl group, a substituted or unsubstituted C3-C30 cycloalkylalkyl group, a substituted or unsubstituted C3-C30 cycloalkenyl group, a substituted or unsubstituted C5-C30 aryl group, a substituted or unsubstituted C5-C30 arylalkyl group, a substituted or unsubstituted C5-C30 heteroaryl group, a substituted or unsubstituted C3-C30 heterocyclic ring, a substituted or unsubstituted C4-C30 heterocyclolalkyl group, a substituted or unsubstituted C6-C30 heteroarylalkyl group, fluorine, a C5-C30 fluoroaryl group, or a hydroxyl group. In one embodiment, the R groups are independently of one another, lower alkyl having up to 8 carbon atoms, particularly preferably lower alkyl having up to 4 carbon atoms, especially lower alkyl having up to 2 carbon atoms. In one embodiment, each of the R groups is a methyl.

Polymers can be formed from a suitable composition comprising the present macromers. The compositions can include the present macromers, optional co-monomers, an initiator, and optionally a crosslinker. In one embodiment, the composition can comprise the present macromers and be substantially free of other comonomers. In one embodiment, the composition comprises a macromer in accordance with the present invention and one or more monomers. The composition can be polymerized and cured to form transparent thin films by known thermal or UV cure techniques, using either thermal initiator or photo initiators in the presence or absence of crosslinking agents. The monomers can be added to the monomer mix to create the mixture prior to polymerization to form the polymers network. Examples of suitable monomers include, but are not limited to, hydrophilic acrylic monomers such as HEMA, dimethylacrylamide (DMA), N-vinyl pyrollidone (NVP), Methacrylic acid (MA) etc. A "prepolymer" is a reaction intermediate polymer of medium molecular weight having polymerizable groups. Thus it is understood that the terms "silicone-containing monomers" and "hydrophilic monomers" include prepolymers. The present invention is also directed to silicone hydrogel films comprising the macromers detailed above. (prepolymer is functionalized polymer. A formulation mixture can have prepolymer/macromer possibly with other monomers and initiator, possibly with crosslinker in)

In one embodiment, a hydrogel can be formed using the macromer with any additional monomers. In one embodiment, a composition for forming a hydrogel comprises the present macromer and an initiator.

The present macromers can be used to form hydrophilic silicone homo/copolymers that produce silicone-hydrogel films having improved surface wettability. The contact lenses produced from the silicone-hydrogel films of the present invention do not require any expensive secondary treatments, like plasma oxidation or plasma coating, to improve wettability. That is, the contact lenses produced from silicone-hydrogel films of the present invention, without secondary treatment, are soft, flexible and inherently wettable and exhibit moderate oxygen permeability.

The polymers of the present invention form a clear, transparent homogeneous single-phase solution that can be cured directly without employing any additional homogenizing solvents, depending on the molecular weight of the present siloxane monomers, which are miscible with hydrophilic hydrogel monomers.

In another embodiment of the present invention, the polymers may be formed into silicone-hydrogel films, via processes known in the art. The silicone-hydrogel films of the present invention are soft, flexible, and highly transparent. Silicone-hydrogel films made from the inventive monomers may exhibit better surface wettability compared to ones made using monomers having linear alkyl linked methacrylated silicone polyether chains. In one embodiment, the present silicone hydrogel films have dynamic advancing contact angles with water in the range of about 100° to about 5°; from about 90° to about 10°; from about 80° to about 20°; even from about 70° to about 30°. In one embodiment, the hydrogel has a contact angle of from about 5° to about 25°. Here as elsewhere in the specification and claims, numerical values can be combined to form new and non-disclosed ranges.

In one embodiment, a hydrogel film formed with the present macromers absorbs about 10 wt. % to 90 wt. % of water; about 20 wt. % to about 80 wt. % of water; about 30 wt. % to about 75 wt. % of water; even about 40 wt. % to about 60 wt. % of water, which can vary depending on the molecular weight of the polyethers. Here as elsewhere in the specification and claims, numerical values can be combined to form new and non-disclosed ranges. The contact angle can also be altered in the defined range by adding wetting agents like poly(vinyl pyrrolidone), poly(vinyl alcohol), and hydroxyalkyl cellulose. The silicone hydrogels produced can also exhibit good mechanical properties (such as low modulus and high tear strength) required for the contact lens application.

Conventional silicone-hydrogel films are generally produced by curing a mixture of hydrophobic silicone monomers and hydrophilic hydrogel monomers in the presence of about 10 to 40 wt. % of solvent, as they are incompatible with each other. However in the current invention, the inventive hydrophilic silicone macromers are found to be miscible with conventional hydrophilic hydrogel monomers (such as HEMA, NVP and DMA) and can form a homogeneous solution suitable to produce silicone-hydrogel films without employing any solvent.

In one aspect, the silicone material is water soluble, and satisfies at least one of the following criteria: (a) 1% of the silicone material in a water solution has a transparency of 80% or greater at a wavelength between 400 to 600 nm; (b) 10% of the silicone material in a water solution has a transparency of 80% or greater at a wavelength between 400 to 600 nm; (c) 50% of the silicone material in a water solution has a transparency of 80% or greater on v between 400 to 600 nm; and/or (d) 1% of the silicone material in a water solution has a cloud point of over 30° C. Transparency can be measured by measuring the absorbance of the solution. Absorbance can be measured using any suitable instrument such as, for example, a UV VIS spectrometer.

The silicone material can also exhibit a low turbidity in a water solution. The turbidity is indicative of the opacity of the solution, with a higher turbidity indicating a more opaque solution. In one embodiment, 1% of the silicone material in a water solution has a turbidity of about 100 NTU (Nephalometric Turbidity Units) or less; 90 NTU or less; 75 NTU or less; 50 NTU or less; even 30 NTU or less. In one embodiment, 1% of the silicone material in a water solution has a turbidity of from about 0.1 to 100 NTU; from about 5 to about 90 NTU. Here, as elsewhere in the specification and claims, numerical values can be combined to form new and non-disclosed ranges. It will be appreciated that the Nephalometric Turbidity Units can be used interchangeably with Formula Turbidity Units (FTU). Turbidity can be determined using any suitable turbidimeter.

As has been stated above, conventional silicone monomers (for example, TRIS) must be mixed with hydrophilic monomers like HEMA in the presence of a solvent to get miscible compositions to make silicone hydrogels. The hydrogel co-monomer used to make silicone-hydrogel copolymers of the present invention can be hydrophilic acrylic monomers such as HEMA, dimethylacrylamide (DMA), N-vinyl pyrollidone (NVP), Methacrylic acid (MA) etc.

The silicone macromers can be provided in a composition for forming a material such as, for example, a hydrogel. In one embodiment, a hydrogel forming composition comprises the silicone macromer. In one embodiment, the composition could comprise 100 weight percent of the macromer. In one embodiment, the hydrogel forming composition comprises from about 0.1 weight percent to about 99.9 weight percent of the macromer; from about 1 weight percent to about 99 weight percent; from about 1 weight percent to about 90 weight percent; from about 10 weight percent to about 80 weight percent; even from about 25 weight percent to about 75 weight percent of the macromer. Optionally, the hydrogel forming composition can comprise a co-monomer in an amount of from about 0.1 weight percent to about 50 weight percent; from about 1 weight percent to about 30 weight percent; even from about 5 weight percent to about 20 weight percent. The hydrogel forming composition can also comprise water. The composition comprise from about 0.1 weight percent to about 90 weight percent of water; from about 1 weight percent to about 70 weight percent; from about 5 weight percent to about 50 weight percent; even from about 10 weight percent to about 30 weight percent of water. It will be appreciated that the components in the hydrogel forming composition will add up to a total of 100 weight percent and the hydrogel can include other components besides the macromer, co-monomer, and/or water as desired for a particular purpose or intended application.

The resulting polymers comprising the hydrophilic silicone macromers may be formed into silicone-hydrogel films, via processes known in the art. Accordingly, the present invention is also directed to medical devices, including, but are not limited to contact lens produced from macromers of the present invention. The monomers/polymers of the present invention can be formed into contact lenses by spincasting processes, as disclosed in U.S. Pat. Nos. 3,408,429 and 3,496,254, cast molding processes, as disclosed in U.S. Pat. Nos. 4,084,459 and 4,197,266, combinations of methods thereof, or any other known method for making contact lenses. Polymerization may be conducted either in a spinning mold, or a stationary mold corresponding to a desired contact lens shape. The lens may be further subjected to mechanical finishing, as occasion demands. Polymerization may also be conducted in an appropriate mold or vessel to form buttons, plates or rods, which may then be processed (e.g., cut or polished via lathe or laser) to give a contact lens having a desired shape.

The relative softness or hardness of the contact lenses fabricated from the resulting polymer of this invention can be varied by decreasing or increasing the number of the activated unsaturated group (such as methacryloxy) on the macromer or by varying the percent of the co-monomer or the crosslinker. Generally, as the ratio of polysiloxane units to activated unsaturated units increases, the softness of the material increases.

The polymers of this invention can also contain ultraviolet absorbents, pigments and colorants or reactive tints in the form of additives or co-monomers.

The oxygen permeability of the hydrogel films or lenses can be tuned from 40 Dk to 100 Dk units; from 50 to 90 Dk units; even from 60 to 80 Dk units by selecting the silicone monomers, independently or in combinations, of the present invention. The monomers and prepolymers employed in accordance with this invention are readily polymerized to form three-dimensional networks, which permit the transport of oxygen with improved wettability along with better mechanicals and optical clarity.

Specific use of the films include intraocular lenses, artificial corneas, and soft daily disposable contact lens, extended wear contact lenses or as coatings for biomedical devices. Articles formed of device forming compositions comprising the macromers of formula (1) with or without any co-monomers. In one embodiment, the article is the polymerization product of a mixture comprising the aforementioned macromer and at least a second monomer. In another embodiment, the composition for forming the hydrogel comprises the present macromer and is substantially free of other co monomers. The invention is applicable to a wide variety of polymeric materials, either rigid or soft. Especially preferred polymeric materials are lenses including contact lenses, phakic and aphakic intraocular lenses and corneal implants although all polymeric materials including biomaterials are contemplated as being within the scope of this invention. Preferred articles are optically clear and useful as a contact lens.

The present invention also provides medical devices comprising or formed from polymers comprising the present silicone macromers. Examples of devices that comprise or be formed from polymers comprising the present macromers include but are not limited to, heart valves and films, surgical devices, vessel substitutes, intrauterine devices, membranes, diaphragms, surgical implants, blood vessels, artificial ureters, artificial breast tissue and membranes intended to come into contact with body fluid outside of the body, e.g., membranes for kidney dialysis and heart/lung machines and the like, catheters, mouth guards, denture liners, ophthalmic devices, and especially contact lenses.

In one aspect the hydrophilic silicone macromer can be used in preparation of homo or copolymers with other free radical polymerization effective monomers to form materials in bulk or latex form. Homopolymers, copolymers, emulsions, and latex particles comprising the inventive macromers can be used as ingredients in personal care formulations including skin care, hair care, and nail care formulations, such as lipsticks, mascaras, foundations, lotions, creams, shampoos, conditioners and nail polishes, to improve their ware, tactile properties and ease of application. They also can be used in textile and fiber treatment applications to impart smooth, soft feel and wettability to both natural and synthetic fibers. Finally the homopolymers, copolymers, emulsion and latex particles can be incorporated into coating formulations for metal, plastic, wood and paper, such as varnishes, latex paints and roofing compositions.

The macromers of the present invention can also be used as internal wetting agents or wettable crosslinkers in a device or article.

Aspects of the invention may be further understood with reference to the following non-limiting examples.

EXAMPLES

Example 1

Water Soluble Macromer

To a 250 ml three-neck round bottom flask is added 52 g of siloxane polyether copolymer, and then 150 ml anhydrous THF via syringe. The flask is set on ice-bath with a magnetic stirrer and nitrogen inlet, and connected to a dry ice condenser, thermometer and a septum. 3.364 g of triethylamine is added to the reaction mixture via a syringe. At close to 0 degree, 2.736 g of acryloyl chloride is slowly added via syringe to the reaction mixture under stirring. After completion of the addition, continue to stir at low temperature for a few hours and thenroom temperature for a few hours. After purification the pale yellow liquid is saved in a refrigerator.

Examples 2-7

Examples 2-7 illustrate formulations employing the macromer of Example 1, and properties of those formulations and results organized in Table 1. The films are casted by placing formulation mix between glass slides and set the glass slides under UV to cure.

Contact angle is evaluated using VCA Optima XE contact angle measurement device from AST, Inc., The measurements are performed by taking fully hydrated film out of water, place the film on glass slide, quickly dry the film surface with Kimwipe, and contact angle is measured.

Water content is evaluated by weighting fully hydrated film and record as A, then sufficiently dry the film in oven and weight the dry film, record as B. Water content is obtained by calculating Water %=100(A−B)/A.

TABLE 1

| | Formulations | | | | | |
|---|---|---|---|---|---|---|
| | 2 | 3 | 4 | 5 | 6 | 7 |
| Example 1 | 100 | 50 | 50 | 60 | 50 | 50 |
| HEMA | | | 10 | | | |
| NVP | | | 20 | 40 | | |
| DMA | | | 20 | | | |
| EGDMA | | | | | | 1 |
| D1173 | 1 | 1 | 1 | 1 | 0.25 | 1 |
| Water | | 50 | | | 50 | 50 |
| Film Clarity | Clear | Clear | Clear | Clear | Clear | Clear |
| Contact angle | 10 | 22 | 14 | 6 | 10 | 10 |
| Water content | 66.2 | 75.1 | 54.5 | 53.1 | 75.2 | 74.1 |
| Extractable | | | 9% | | | |

Example 8

To a three-neck 500 ml round bottom flask equipped with a heating mantle, mechanical stirrer, condenser, thermo couple and nitrogen inlet was added 8.12 grams of hexamethyldisiloxane, 289.85 grams of octamethylcyclotetrasiloxane (D4), 107.27 grams of siloxane hydride polymer, and 1.92 grams of Filtrol-20. The reaction mixture temperature was slowly increased to 100° C. and refluxed for 6 hours under stirring. In the end, vacuum filtration is applied to remove the solid, and the filtrate is heated under vacuum to remove the volatiles. 346.1 grams of siloxane hydride was obtained.

Example 9

To a 300 ml three-neck round bottom flask equipped with a heating mantle, condenser, nitrogen inlet, magnetic stirrer, and thermal couple was added 9.5 grams of allyl polypropyleneglycol (APPG-800R), 33.6 grams of allyl polyethyleneglycol (APEG-550-OAc), and 0.143 grams of a platinum catalyst solution. 15.1 grams of siloxane hydride from example 8 and 9.1 grams of isopropyl alcohol (IPA) were mixed and slowly added to the solution in the reaction flask while slowly heating. The solution is refluxed at 87° C. until all hydride is consumed. Ultrafiltration is conducted to purify the product, and 41.75 grams of product is recovered.

Example 10

To a 250 ml three-neck round bottom flask equipped with an ice-bath, magnetic stirrer, nitrogen inlet, and thermometer was added 26.65 grams of purified product from example 9, 50 ml of anhydrous tetrahydrofuran (THF), and 0.78 grams of triethylamine 0.72 grams of methacryloyl chloride was slowly added under stirring. The mixture was stirred under nitrogen for 4 hours from 0° C. to 10° C., and then filtered through a filter pad and rotavap to remove solvent and give the product. The resulting polymer is soluble in water. Solutions of 1%, 10%, and 50% by weight of polymer in deionization water solution was made. FIG. 1 shows the UV Vis spectra of these solutions.

Example 11

To a 500 ml three-neck round bottom flask equipped with an ice bath, magnetic stirrer, and nitrogen inlet was added 213.7 grams of allyl polyethyleneglycol (APEG550-0H), 39.64 grams of dihydropyran, and 0.918 grams of toluenesulfonic acid. The mixture was stirred under nitrogen overnight. 0.43 grams of potassium carbonate was added and the solution was stirred at room temperature for 5 hours. The solution was filtered through a filter pad and then vacuum filtered to remove solvent. 239.58 grams of product was obtained.

Example 12

To a three-neck 250 ml round bottom flask equipped with a nitrogen inlet, magnetic stirrer, heating mantle, condenser, and thermo-couple was added 19.64 grams of siloxane hydride, 29.0 grams of isopropyl alcohol, and 0.01 grams of Armeen M2C. The mixture was slowly heated under nitrogen and stirring. 2.49 grams of allyl glycidyl ether and 0.03 grams of platinum catalyst solution was slowly added to the reaction flask via syringe while increasing the temperature. The mixture was refluxed at 82° C. for 1 hour. 0.133 grams of platinum catalyst solution and 48.8 grams of product from example 11 was mixed in an addition funnel with slow addition to the flask and refluxed at 88° C. for 4 hours.

Example 13

To a 300 ml three-neck round bottom flask equipped with a heating mantle, condenser, magnetic stir, thermo-couple, and nitrogen inlet was added 20.1 grams of isopropyl alcohol, 0.0136 grams of TEMPO inhibitor (2,2,6,6-tetramethylpiperidene-1-yl)oxy, and 2.07 grams dimethylaminopropyl methacrylamide 0.71 grams of acetic acid is slowly added to the mixture under stirring and heated up to 50° C. 46.45 grams of the reaction mixture of example 12 is slowly added over 10 minutes, and the mixture is heated for 2 hours after complete addition. Vacuum stripping is conducted to remove solvent and give the crude product.

Example 14 and Example 15

Formulation work was done using the prepolymer from Example 10. Films were prepared according to the formulations in Table 2. The films obtained were optically clear.

TABLE 2

| Number | Example 14 | Example 15 |
|---|---|---|
| Example 10 | 50 | 70 |
| HEMA | 20 | 0 |
| DMA | 25 | 20 |
| NVP | 5 | 10 |
| EGDMA | 1 | 0.5 |
| D-1173 | 1 | 1 |
| Water | 0 | 5 |
| Extractables (%) | 20.9 | 40.5 |
| Water content (%) | 70.1 | 78.1 |
| Contact angle | 83 | 83 |
| Modulus (Mpa) | 0.77 | 0.49 |

While the invention has been described with reference to a preferred embodiment, those skilled in the art will understand that various changes may be made and equivalents may be substituted for elements thereof without departing from the scope of the invention. It is intended that the invention not be limited to the particular embodiment disclosed as the best mode for carrying out this invention, but that the invention will include all embodiments falling within the scope of the appended claims. All citations referred herein are expressly incorporated herein by reference.

What is claimed is:

1. A macromer comprising:
a siloxane backbone;
a graft attached to the siloxane backbone, the graft comprising a polymerizable functional group; and
a concentration of grafts comprising hydrophilic groups sufficient to render the macromer at least partially hydrophilic, wherein the macromer is of the Formula (1):

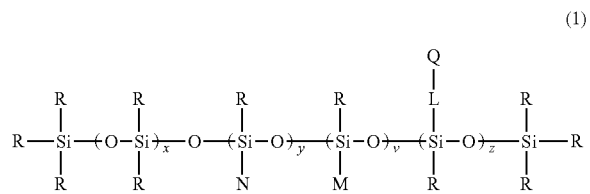

where M is a polymeric hydrophilic group or segment chosen from a polyvinyl alcohol (PVA), a polyamide, a polyimide, a polylactone, a homopolymer of a vinyl lactam, a copolymer of at least one vinyl lactam in the presence or in the absence of one or more vinylic comonomers, a homopolymer of acrylamide, a homopolymer of methacrylamide, a copolymer of acrylamide with one or more hydrophilic vinylic monomers, a copolymer methacrylamide with one or more hydrophilic vinylic monomers, polyethylene glycol, a poly-N--N dimethylacrylamide, a polyacrylic acid, a poly-2-ethyl oxazoline, a heparin polysaccharides, a polysaccharide, or a combination of two or more thereof; L is a hydrophilic or hydrophobic linkage; N is a hydrophilic or hydrophobic group or segment; Q is a polymerizable functional group; x is zero or an integer greater than zero; y is zero or an integer greater than zero; v is an integer greater than zero; and z is greater than zero; when the L group is a hydrophilic linkage, L can be the same as or different than the hydrophilic M group; R is independently hydrogen, a straight or branched C1-C30 alkyl group, a C1-C30 fluoroalkyl group, a C1-C20 ester-containing group, an alkyl ether, cycloalkyl ether, cycloalkenyl ether, aryl ether, arylalkyl ether, a polyether-containing group, a C1-C30 alkoxy group, a C3-C30 cycloalkyl group, a C3-C30 cycloalkylalkyl group, a C3-C30 cycloalkenyl group, a C5-C30 aryl group, a C5-C30 arylalkyl group, a C5-C30 heteroaryl group, a C3-C30 heterocyclic ring, a C4-C30 heterocyclolalkyl group, a C6-C30 heteroarylalkyl group, fluorine, a C5-C30 fluoroaryl group, or a hydroxyl group.

2. The macromer of claim 1, wherein L is chosen from a bond, a straight or branched C1-C30 alkylene group, a C1-C30 fluoroalkylene group, a C1-C20 ester-containing group, an alkylene ether, cycloalkylene ether, cycloalkenylene ether, arylene ether, arylalkylene ether, a polyether-containing group, a C1-C30 alkenoxy group, a C3-C30 cycloalkylene group, a C3-C30 cycloalkylalkylene group, a C3-C30 cycloalkenylene group, a C5-C30 arylene group, a C5-C30 arylalkylene group, a C5-C30 heteroarylene group, a divalent C3-C30 heterocyclic ring, a C4-C30 heterocyclolalkylene group, a C6-C30 heteroarylalkylene group, a C5-C30 fluoroarylene group, a hydroxyl substituted alkylene ether, a divalent C3-C30 cationic moiety containing group; or combinations of two or more thereof.

3. The macromer of claim 1, wherein Q is chosen from acrylate-containing radicals, methacrylate-containing radicals, acrylamide-containing radicals, methacrylamide-containing radicals, vinyl-containing radicals, allyl-containing radicals, methallyl-containing radicals, styrene-containing radicals, internal olefinic bond containing molecules, or a combination of two or more thereof.

4. The macromer of claim 3, wherein Q is chosen from vinylcarbonate-containing radicals, vinylcarbamate-containing radicals, butenedioic acid, butenedioic esters or amides, itaconic acid, itaconic acid esters or amides, or a combination of two or more thereof.

5. The macromer of claim 1, wherein N is chosen from a straight or branched C1-C30 alkyl group, a C1-C30 fluoroalkyl group, a C1-C20 ester-containing group, an alkyl ether, cycloalkyl ether, cycloalkenyl ether, aryl ether, arylalkyl ether, a polyether-containing group, a C1-C30 alkoxy group, a C3-C30 cycloalkyl group, a C3-C30 cycloalkylalkyl group, a C3-C30 cycloalkenyl group, a C5-C30 aryl group, a C5-C30 arylalkyl group, a C5-C30 heteroaryl group, a C3-C30 heterocyclic ring, a C4-C30 heterocyclolalkyl group, a C6-C30 heteroarylalkyl group, a C5-C30 fluoroaryl group, a hydroxyl substituted alkyl ether, a C3-C30 cationic moiety containing group; or combinations of two or more thereof.

6. The macromer of claim 1, wherein M comprises polyethylene glycol, and Q is a methacrylate group.

7. The macromer of claim 1, wherein z is 1 to about 200, x is 0 to about 1000, and y is 0 to about 200.

8. The macromer of claim 1, where N and M are hydrophilic groups, optionally where N and M are the same.

9. The macromer of claim 1, wherein the macromer is water soluble, and satisfies at least one of the following criteria:
   (a) 1% of the macromer in a water solution has a transparency of 80% or greater at a wavelength between 400 to 600 nm;
   (b) 10% of the macromer in a water solution has a transparency of 80% or greater at a wavelength between 400 to 600 nm;
   (c) 50% of the macromer in a water solution has a transparency of 80% or greater at a wavelength between 400 to 600 nm; and/or
   (d) 1% of the macromer in a water solution has a cloud point of over 30 C.

10. The macromer of claim 1, wherein a solution of 1% by weight of the macromer in water has a turbidity of about 100 NTU or less.

11. A hydrogel forming composition comprising a macromer comprising:
   a siloxane backbone;
   a graft attached to the siloxane backbone, the graft comprising a polymerizable functional group; and
   a concentration of grafts comprising hydrophilic groups sufficient to render the macromer at least partially hydrophilic, wherein the macromer is of the Formula (1):

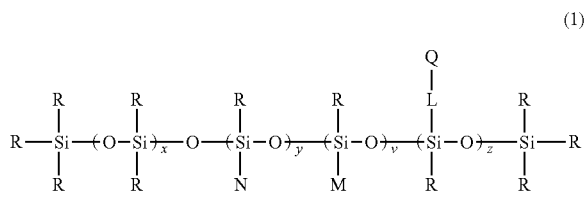

where M is a polymeric hydrophilic group or segment L is a hydrophilic or hydrophobic linkage; N is a hydrophilic or hydrophobic group or segment. Q is a polymerizable functional group; x is zero or an integer greater than zero; y is zero or an integer greater than zero; v is an integer greater than zero; and z is greater than zero; when the L group is a hydrophilic linkage, L can be the same as or different than the hydrophilic M group; R is independently hydrogen, a straight or branched C1-C30 alkyl group, a C1-C30 fluoroalkyl group, a C1-C20 ester-containing group, an alkyl ether, cycloalkyl ether, cycloalkenyl ether, aryl ether, arylalkyl ether, a polyether-containing group, a C1-C30 alkoxy group, a C3-C30 cycloalkyl group, a C3-C30 cycloalkylalkyl group, a C3-C30 cycloalkenyl group, a C5-C30 aryl group, a C5-C30 arylalkyl group, a C5-C30 heteroaryl group, a C3-C30 heterocyclic ring, a C4-C30 heterocyclolalkyl group, a C6-C30 heteroarylalkyl group, fluorine, a C5-C30 fluoroaryl group, or a hydroxyl group;
wherein the composition comprises from about 0.1 to about 90 weight percent of water.

12. The hydrogel forming composition of claim 11 further comprising a co-monomer, wherein the co-monomer comprises hydroxyethyl methacrylate, N-vinyl-2-pyrrolidone, N,N-dimethylacrylamide, methacrylic acid, glycerol methacrylate, or a combination of two or more thereof.

13. The hydrogel forming composition of claim 12, wherein the hydrogel forming composition comprises from about 0.1 weight percent to about 99.9 weight percent of the macromer.

14. A hydrogel formed from the composition of claim 11.

15. The hydrogel of claim 14, having a contact angle with water of from about 100° to about 5°.

16. The hydrogel of claim 14, having a water absorption of about 10 wt. % to about 90 wt. %.

17. An article comprising the hydrogel of claim 14.

18. The article of claim 17, wherein the article is chosen from a heart valve, a film, a surgical device, a vessel substitute, a intrauterine device, a membrane, a diaphragm, a surgical implant, a blood vessel, and artificial ureter, artificial breast tissue, a membranes for kidney dialysis, or membrane for a heart/lung machine, a catheter, a mouth guard, a denture liner, an ophthalmic device, or a contact lens.

19. An article comprising an internal wetting agent or a wettable crosslinker, the internal wetting agent and/or wettable crosslinker comprising the macromer of claim 1.

20. The macromer of claim 1, wherein M is polyethylene glycol, Q comprises a methacrylate group, L is polyethylene glycol, N is polyethylene glycol, R comprises a lower alkyl having up to 8 carbon atoms, z is 1 to about 200, x is 0 to about 1000, v is 2 to about 200, and y is 0 to about 200.

* * * * *